US010575930B2

(12) United States Patent
Krastev (10) Patent No.: US 10,575,930 B2
(45) Date of Patent: Mar. 3, 2020

(54) OSTEOTOME SET FOR DENTAL IMPLANT SOCKET FORMATION WITH ALTERNATING BASE AND CRESTAL WORK AREAS

(71) Applicant: Pavel Krastev, New Hyde Park, NY (US)

(72) Inventor: Pavel Krastev, New Hyde Park, NY (US)

(*) Notice: Subject to any disclaimer, the term of this patent is extended or adjusted under 35 U.S.C. 154(b) by 119 days.

(21) Appl. No.: 15/936,693

(22) Filed: Mar. 27, 2018

(65) Prior Publication Data

US 2018/0289452 A1 Oct. 11, 2018

Related U.S. Application Data

(60) Provisional application No. 62/482,748, filed on Apr. 7, 2017.

(51) Int. Cl.
*A61C 8/00* (2006.01)
*A61C 1/16* (2006.01)
*A61B 17/16* (2006.01)

(52) U.S. Cl.
CPC .............. *A61C 8/0089* (2013.01); *A61C 1/16* (2013.01); *A61B 17/1604* (2013.01); *A61B 17/1673* (2013.01)

(58) Field of Classification Search
CPC ....... A61C 8/00; A61C 8/0089; A61C 8/0092; A61C 1/10; A61C 1/12; A61B 17/16; A61B 17/1673
See application file for complete search history.

(56) References Cited

U.S. PATENT DOCUMENTS

| 1,279,495 A | 9/1918 | Dom |
| 2,984,241 A | 5/1961 | Carlson |
| 3,678,934 A | 7/1972 | Warfield |

(Continued)

OTHER PUBLICATIONS

Summers, Robert B, DMD, "A New Concept in Maxillary Implant Surgery: The Osteotome Technique"; Compend. Contin. Educ. Dent., vol. XV, No. 2; 1994; 6 pages.

(Continued)

*Primary Examiner* — Christopher J Beccia
(74) *Attorney, Agent, or Firm* — Thomas A. O'Rourke; Bodner & O'Rourke, LLP (57) ABSTRACT

A number of osteotomes, n, form a set of osteotomes, for use during a ridge expansion osteotomy to reduce alveolar stress and to reduce likelihood of a fracture, with each osteotome of the set having a conical working tip with a free end having a diameter $\phi_{An}$, and a working base $\phi_{Bn}$; a first osteotome, n=1, of the set has the working tip formed with a first diameter, $\phi_{A1}$=Y, at the free end, and with a second diameter, $\phi_{B1}$=X, at the working base, the second diameter being larger than the first diameter, X>Y; and wherein for successive osteotomes of the set, the diameter at the free end increases as an alternate step and regressive step sequence, and the diameter at the working base alternately increases by a constant increment c, as a step function.

20 Claims, 9 Drawing Sheets

(56) References Cited

U.S. PATENT DOCUMENTS

| | | |
|---|---|---|
| 3,986,512 A | 10/1976 | Walliser |
| 4,112,944 A | 9/1978 | Williams |
| 4,150,675 A | 4/1979 | Comparetto |
| 4,412,825 A | 11/1983 | Tokarz |
| 4,600,005 A | 7/1986 | Hendel |
| 4,673,353 A | 6/1987 | Nevin |
| 4,881,534 A | 11/1989 | Uhl |
| 5,049,125 A | 9/1991 | Accaries |
| D324,424 S | 3/1992 | Michelson |
| 5,188,488 A | 2/1993 | Nakayama |
| D338,528 S | 8/1993 | Koros |
| D342,313 S | 12/1993 | Hood |
| 5,291,914 A | 3/1994 | Bares |
| 5,312,255 A | 5/1994 | Bauer |
| 5,584,688 A | 12/1996 | Sakuma |
| 5,722,977 A | 3/1998 | Wilhelmy |
| 5,915,967 A | 6/1999 | Clokie |
| 5,997,298 A * | 12/1999 | Nowak .............. A61B 17/1604 433/165 |
| 6,171,312 B1 | 1/2001 | Beaty |
| 6,200,289 B1 | 3/2001 | Hochman |
| D450,844 S | 11/2001 | Lewis |
| 6,485,495 B1 | 11/2002 | Jenkinson |
| 6,537,280 B2 | 3/2003 | Dinger |
| 6,790,211 B1 | 9/2004 | McPherson |
| 6,899,715 B1 | 5/2005 | Beaty |
| 7,100,476 B1 | 9/2006 | Feit |
| 7,125,253 B2 | 10/2006 | Kitamura |
| 7,217,130 B2 | 5/2007 | Giorno |
| 7,241,144 B2 * | 7/2007 | Nilo .................. A61C 8/0089 433/141 |
| 7,396,232 B2 | 7/2008 | Fromovich |
| 7,547,210 B1 | 6/2009 | Valen |
| 7,632,280 B2 | 12/2009 | Hochman |
| 7,771,199 B2 | 8/2010 | Hochman |
| 8,029,284 B2 | 10/2011 | Better |
| 8,083,747 B2 | 12/2011 | Song |
| D653,339 S | 1/2012 | Ross |
| 8,282,640 B2 | 10/2012 | Hung |
| 8,480,675 B2 | 7/2013 | Betts |
| 9,011,446 B1 | 4/2015 | Henderson |
| 9,028,253 B2 | 5/2015 | Huwais |
| 9,198,743 B2 | 12/2015 | Wang |
| 9,289,218 B2 | 3/2016 | Courtney |
| 9,326,778 B2 | 3/2016 | Huwais |
| 9,333,058 B1 * | 5/2016 | Krastev .............. A61C 8/0089 |
| 9,421,028 B2 | 8/2016 | Darian |
| 9,498,308 B1 | 11/2016 | Krastev |
| 9,526,593 B2 | 12/2016 | Huwais |
| 9,603,720 B2 | 3/2017 | Kelley |
| 2002/0094508 A1 | 7/2002 | Lorenzi |
| 2003/0228556 A1 | 12/2003 | Giorno |
| 2006/0020326 A9 | 1/2006 | Bokluc |
| 2006/0172255 A1 | 8/2006 | Hochman |
| 2006/0271056 A1 | 11/2006 | Terrill-Grisoni |
| 2007/0042326 A1 | 2/2007 | Cardoso |
| 2007/0055257 A1 | 3/2007 | Vaccaro |
| 2007/0293871 A1 | 12/2007 | Ackermann |
| 2008/0188878 A1 | 8/2008 | Young |
| 2008/0215010 A1 | 9/2008 | Silver |
| 2008/0275379 A1 | 11/2008 | Kurrek |
| 2008/0319466 A1 | 12/2008 | Eder |
| 2009/0042158 A1 | 2/2009 | Steiner |
| 2009/0274996 A1 | 11/2009 | Miller |
| 2009/0292288 A1 | 11/2009 | Hung |
| 2009/0326440 A1 | 12/2009 | Lee |
| 2010/0196841 A1 | 8/2010 | Nahlieli |
| 2010/0221681 A1 | 9/2010 | Hochman |
| 2010/0291511 A1 | 11/2010 | Lee |
| 2010/0324561 A1 | 12/2010 | Watzek |

OTHER PUBLICATIONS

Summers, Robert B, DMD, "The Osteotome Technique: Part 2—The Ridge Expansion Osteotomy (REO) Procedure"; Compend. Contin. Educ. Dent., vol. XV, No. 24 1994; 7 pages.

Vladimir Koifman, "Fraunhofer Institute and Awaiba Developed 1 mm>3 Camera," Image Sensors World, News and Discussions about Image Sensors, Mar. 11, 2011.

Muronoi M, er al., "Simplified procedure for augmentation of the sinus floor using a haemostatic nasal balloon," British J of Oral & Maxillofacial Surgery 41(2):120-121, 2003.

Hernandez-Alfaro F, sr al., Prevalence and management of Schneiderian membrane perforations during sinus-lift procedures. Clin. Oral Impl. Res. 19, 2008; 91-98.

Javier Ferrer, et. al. , "Analysis of the Use of Expansion Osteotomes for the Creation of Implant Beds . . . echnical Contributions and and Review of the Literature," 2006.

Laksman Dene; Ridge Expansion and Immediate Implant Placement in the Esthetic Zone; NYSDY; Mar. 2010; 4 pages.

* cited by examiner

FIG. 4
(Flexible Osteotome Set with Summer's Diameter Escalation)

FIG. 4A

(Flexible Osteotome Set with Summer's Diameter Escalation)

OSTEOTOME SET FOR DENTAL IMPLANT SOCKET FORMATION WITH ALTERNATING BASE AND CRESTAL WORK AREAS

CROSS REFERENCES TO RELATED APPLICATIONS

This application claims priority on U.S. Provisional Application Ser. No. 62/482,748 filed on Apr. 7, 2017, the disclosures of which are incorporated herein by reference.

FIELD OF THE INVENTION

The present invention relates to improvements in an osteotome set that can be used in a variety of procedures, including, but not limited to ridge expansion, bone densification, ridge splitting, crestal sinus elevation, etc., and more particularly relates to a series of osteotome tips that cause less stress and a correspondingly reduced tendency toward fracturing of the alveolar ridge.

BACKGROUND OF THE INVENTION

There are many conditions which may result in a person becoming partially or completely edentulous (periodontal disease, an injury, etc.), which is commonly remedied today by dental implants. Denial implants are endosseous, being a "root" device that is usually made of titanium, where the implants are inserted into the jaw through the bone at the alveolar ridges, after which a healing period on the order of months is necessary for osseointegration. During this healing period the bone will grow in and around the implant to provide support.

The alveolar ridges are columns of bone, found on both the maxilla and the mandible, that surround and anchor the teeth within sockets known as alveoli. However, the alveolar bone quickly becomes atrophic in the absence of teeth, typically resulting in lack of sufficient bone mass for successful implantation. In the Maxilla, when sinus pneumatization decreases available bone after tooth loss, a sinus elevation procedure prior to implant placement is required to increase the amount of bone therein. The sinus lift procedure may be performed either through a lateral approach or a crestal approach.

In the crestal approach for a sinus lift procedure of the posterior maxilla (upper jaw), to which the improvements of the present invention is directed, a pilot drill may initially be used to create a small hole in the crestal cortex to reach the cancellous layer, and to form an implant insertion axis. The anatomical characteristics of the posterior maxilla, particularly the existence of its more spongy (cancellous) bone, enable it to successfully lend itself to undergo the ridge expansion osteotomy technique developed by R. B. Summers (see e.g., Summers, DMD, Robert B, "A New Concept in Maxillary Implant Surgery: The Osteotome Technique;" 1994; Summers, DMD, Robert B, "The Osteotome Technique: Part 2—The Ridge Expansion Osteotomy (REO) Procedure;" 1994; and Summers, DMD, Robert B, "The Osteotome Technique: Part 3—Less Invasive Methods of Elevating the Sinus Floor;" 1994).

The technique causes expansion of the pilot hole without further elimination of bone material, and generally tends to compresses the bone and increases bone density, in the surgeon's favor. The technique uses a succession of conical expansion Osteotome tools having a gradual diameter escalation. The smallest caliber expansion Osteotome tool is inserted manually into the pilot hole, with pressing and rotating of the tool occurring until the desired depth is reached, or until further penetration is resisted, at which time gentle tapping using a surgical mallet on the Osteotome may cause it to reach the proper depth. Further use of successively larger Osteotome tools causes lateral compression that increases bone density and the size of the opening. The procedure is typically carried out by an oral surgeon using different calibers of Osteotomes that are constructed such that the initial diameter of a successively larger Osteotome is the same as the largest penetrating diameter of the previous conical Osteotome that was used, thereby providing a constant progression of increasing separation.

The procedure exhibits high success rates if the sinus membrane was not breached during the procedure, as discussed in the article by Hernandez-Alfaro F, Torradeflot M M, and Marti C., titled "Prevalence and Management of Schneiderian Membrane Perforations during Sinus-lift Procedures." But a further consideration for the success of the implant concerns the impact of the Summers' diameter escalation on the crest of the alveolar ridge, when the ridge has undergone resorption producing a knife-edged shape, rather than its tall, rounded shape. The present invention offers various improvements to aid the oral surgeon, including Osteotome configurations and a method of use that reduce fracturing of either proximate to the base or proximate to the crest of the alveolar ridges during the osteotomy.

OBJECTS OF THE INVENTION

It is an object of the invention to provide a series of Osteotomes that are constructed to perform a ridge expansion osteotomy.

It is another object of the invention to provide a series of ridge expansion osteotomes that are particularly adapted to reduce the possibility of fracture.

It is a further object of the invention to provide a series of ridge expansion osteotomes that are particularly adapted to alternately cause modest base expansion and crestal expansion during socket formation, for each successive pair of osteotomes in the set that are used.

It is another object of the invention to provide a double-ended osteotome set and a corresponding impact cap to reduce the required number of tools per set.

It is a further object of the invention to provide a set of osteotomes that include flexible tips.

Further objects and advantages of the invention will become apparent from the following description and claims, and from the accompanying drawings.

BRIEF DESCRIPTION OF THE DRAWINGS

The description of the various example embodiments is explained in conjunction with appended drawings, in which.

DETAILED DESCRIPTION OF THE INVENTION

As used throughout this specification, the word "may" is used in a permissive sense (i.e., meaning having the potential to), rather than the mandatory sense (i.e., meaning must). Similarly, the words "include", "including" and "includes" mean including but not limited to.

The phrases "at least one", "one or more", and "and/or" are open-ended expressions that are both conjunctive and disjunctive in operation. For example, each of the expressions "at least one of A, B and C", "one or more of A, B, and C", and "A, B, and/or C" mean all of the following possible combinations: A alone; or B alone; or C alone; or A and B together; or A and C together; or B and C together; or A, B and C together.

Also, all references (e.g., patents, published patent applications, and non-patent literature) that are cited within this document are incorporated herein in their entirety by reference.

Furthermore, the described features, advantages, and characteristics of any particular embodiment disclosed herein, may be combined in any suitable manner with any of the other embodiments disclosed herein.

Figures 1, 1A:
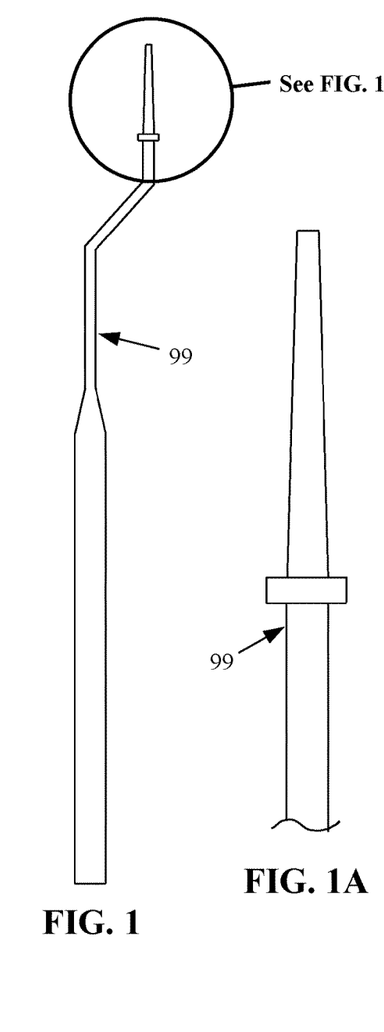
FIG. 1 illustrates an osteotome.
FIG. 1A illustrates an enlarged detail view of the end of the osteotome of FIG. 1.

FIG. 1 shows a prior art osteotome 99 that has traditionally been used for providing expansion and compaction of bone surrounding an implant pilot hole formed in an alveolar ridge during a sinus lift procedure. FIG. 1A shows and enlarged detail view of the tip of the osteotome of FIG. 1.

Figure 2:
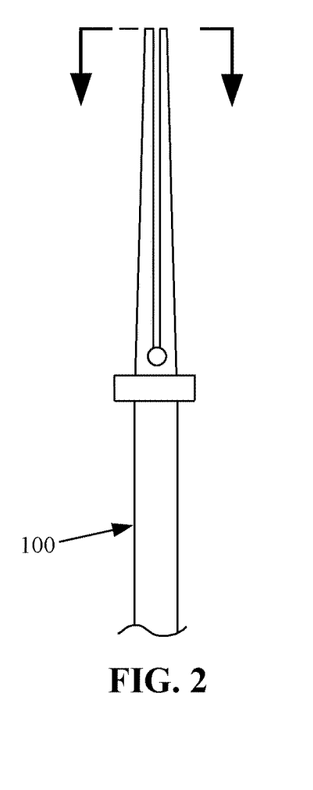
FIG. 2 illustrates a side view of the end of an osteotome in accordance with a first embodiment of the present invention.
Figure 2A:
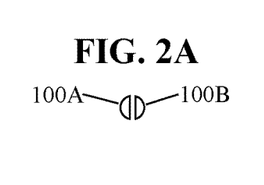
FIG. 2A is an end view of the tip of the osteotome embodiment shown in FIG. 2.
Figure 3:
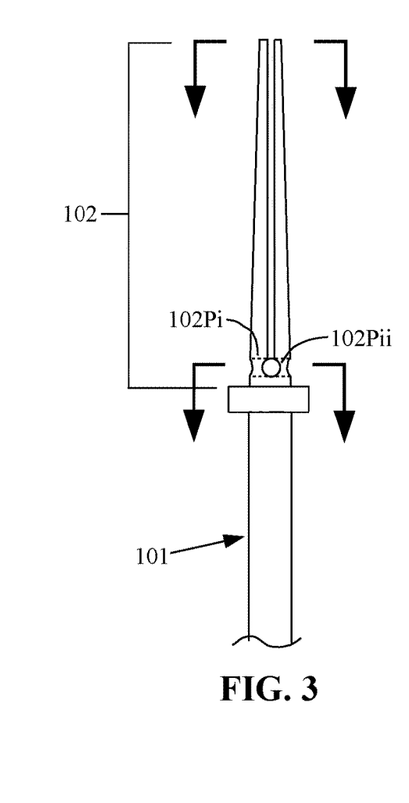
FIG. 3 illustrates a side view of the end of an osteotome in accordance with a second embodiment of the present invention.
Figure 3A:
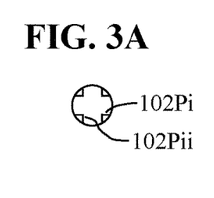
FIG. 3A is an end view of the tip of the osteotome embodiment shown in FIG. 3.
Figure 3B:
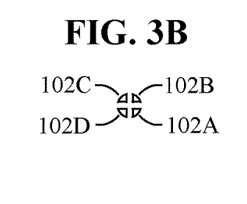
FIG. 3B is a section view taken at the base of the tip of the osteotome shown in FIG. 3.
Figure 4:
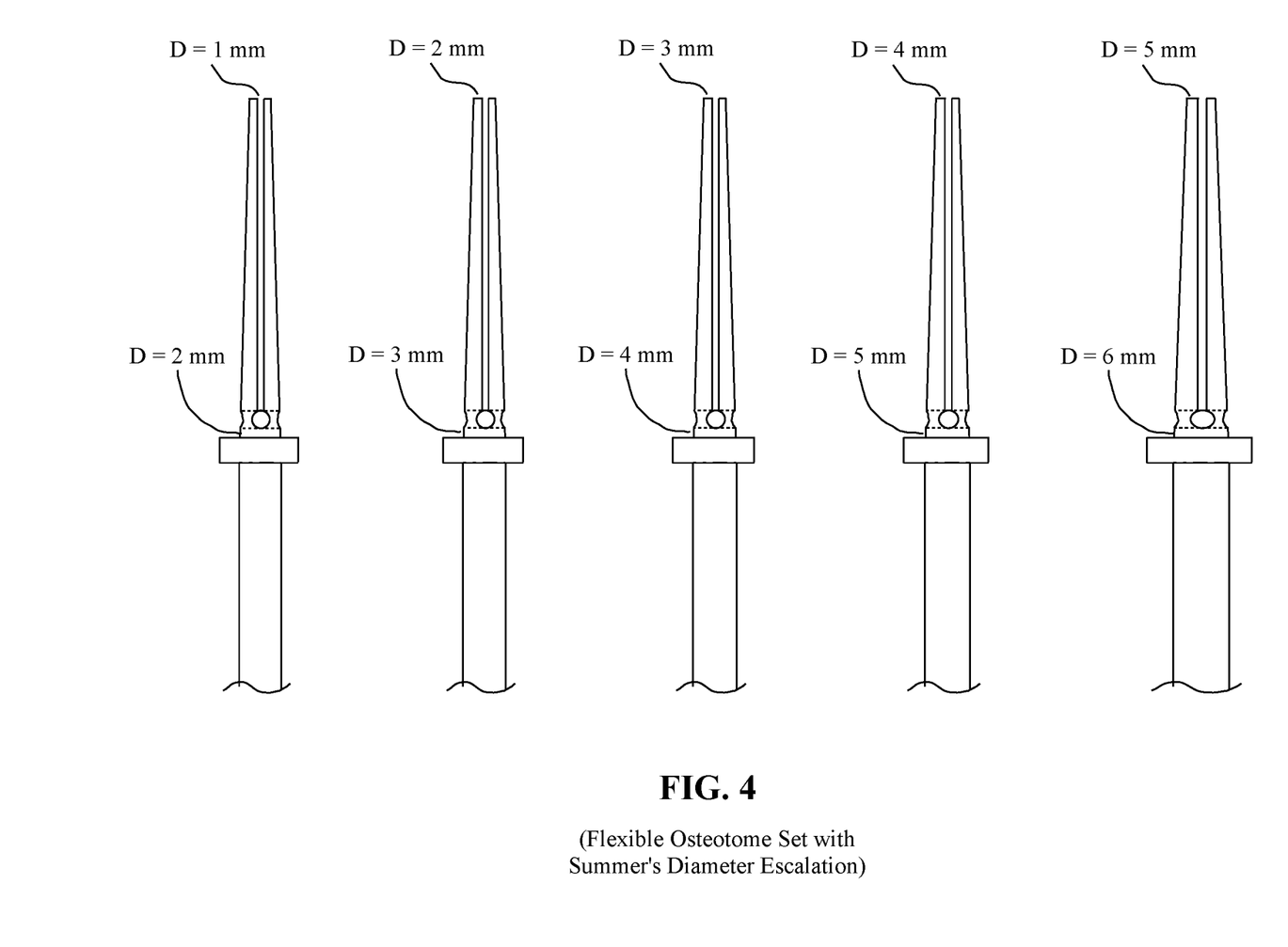
FIG. 4 illustrates a set of osteotomes with flexible tips constructed in accordance with FIGS. 2 and 3, and with the osteotome set exhibiting a nominal Summers' diameter escalation.

An osteotome 100 configuration in accordance with an embodiment of the present invention is shown in FIGS. 2-2A. As seen in the side view of FIG. 2, the tip of the osteotome 100 may be formed with a cross-cut, which may be formed to be substantially parallel to the axial direction of the tip, so that it permits a degree of inward flexing of the resulting two tip portions 100A/100B. In another embodiment, at least two pairs of cross-cuts may be used, as seen in the end view of FIG. 3B, to form the resultant tip portions 102A, 102B, 102C, and 102D. The exterior surface of each of the tip portions 102A, 102B, 102C, and 102B may still be conical, and any desired diameter escalation scheme may be used for the diameter at the free end, and the diameter at the base of the tip 102. Merely to be exemplary, FIG. 4 illustrates a set of osteotomes formed with the above-described cross-cut for each of the tips, and which utilizes a prior art Summers' diameter escalation scheme. As seen in FIG. 3 and thesection view of FIG. 3B, the end of the cross-cuts may terminate proximate to the base of the tip at an orifice, which may be a through-hole. The through-hole may have a radius being substantially larger than the opening formed by the cross-cut, being between 25% and 100% larger than the width shown for the cross-cut opening, in one embodiment, and being between 100% and 200% larger than the width in another embodiment. The through-hole may also be sized to locally reduce the cross-sectional area of the tip by between 50% and 85%. An elliptically-shaped or other shaped orifice may alternatively be used. An enlarged orifice may be formed, for each of the cross-cuts (i.e., where a pair of cross-cuts are used, a first orifice 102Pi and a second orifice 102 Pii may correspondingly be used—see FIG. 3A). The enlarged orifices may be formed proximate to the full working depth of the tip, as shown for the osteotome set in FIG. 4.

To enable greater flexure at the base of the tip, the cross-cuts may extend to orifices that may be formed at a substantial distance beyond the full desired working depth of the tip (see FIG. 4A), and a spacer may be used to limit the extent to which the tip may be inserted into the alveolar socket, to be limited to that intended working depth.

Figure 4A:
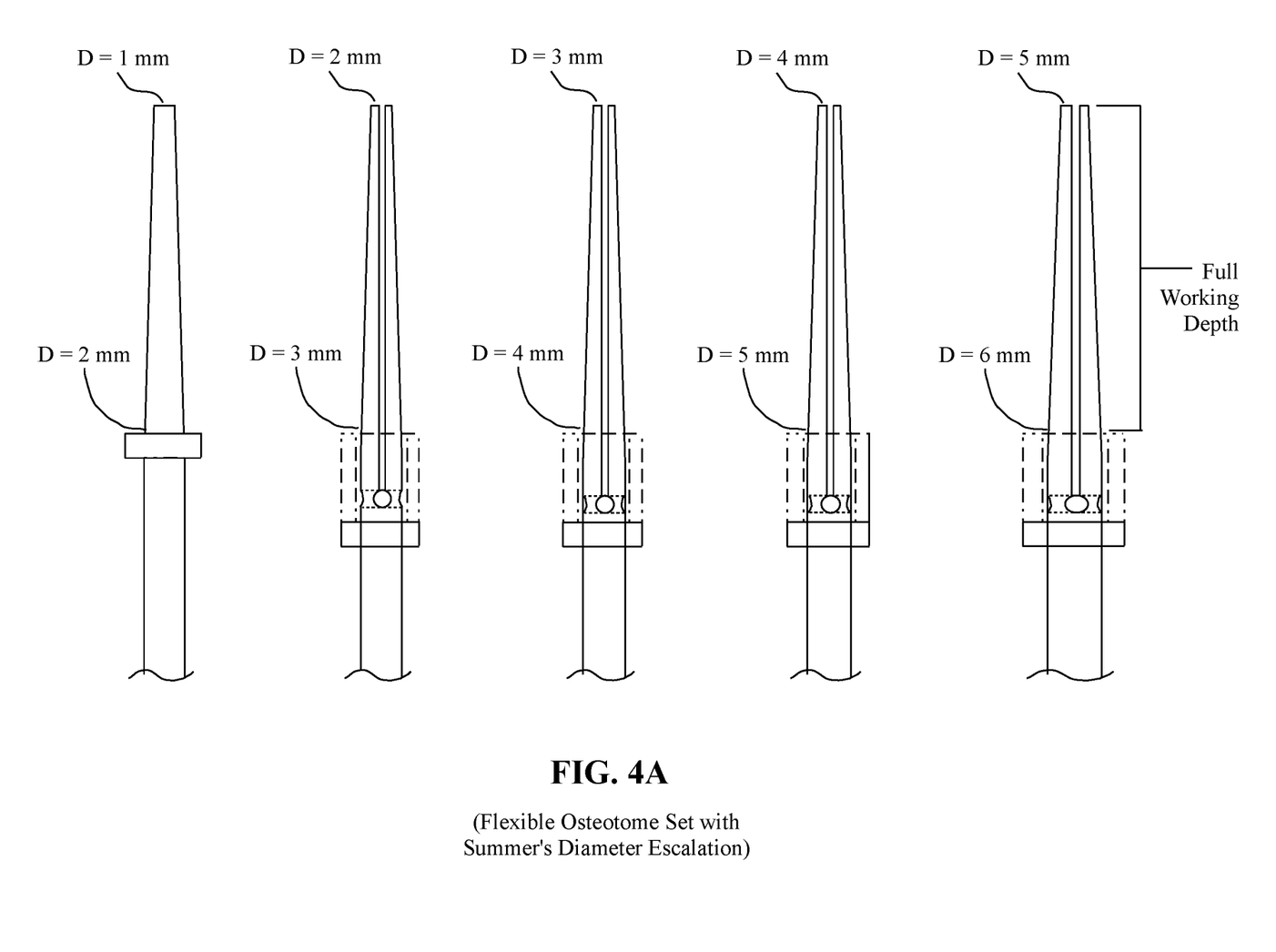
FIG. 4A illustrates a set of osteotomes with flexible tips constructed in accordance with an alternate embodiment, where each of the tips are configured to flex beyond its maximum working depth.

The flexure provide by the cross-cuts in the tips of these osteotome embodiments serves to reduce stress on alveolar ridge during socket formation. In one embodiment, as shown in FIG. 4A, the first osteotome in the set may be formed without the cross-cut, and all the rest of the osteotomes in the set may be formed with the cross-cuts.

Note that use of the cross-cuts on the osteotomes in the set may, for some patient's, tend to require the use of an additional number of osteotomes in the set to produce the final properly sized implant socket.

In an alternate embodiment, every other osteotome in the set of osteotomes may be formed with the cross-cuts. In one embodiment, the diameter escalation scheme utilized may progress (i.e., may only increase) for alternate osteotomes in the set, such that any diametrical increase may occur on an osteotome with the cross-cuts, and the successive osteotome in the set, being without the cross-cuts, may be formed with the same diameter (i.e., no escalation), and may serve to further develop the socket opening that may have only been partially compressed/formed by the previous (cross-cut) osteotome.

Figure 5:
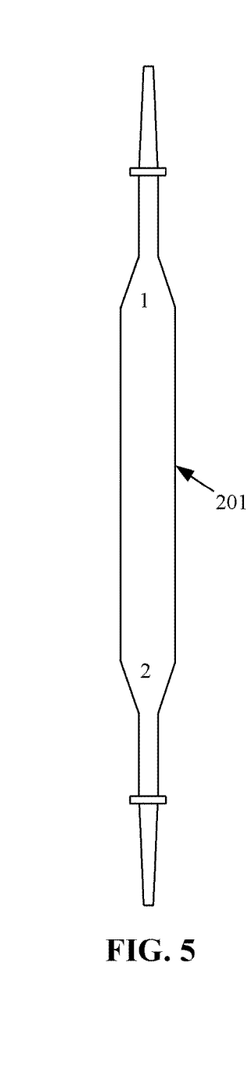
FIG. 5 illustrates a first double-ended osteotome of a set of double-ended osteotomes.
Figure 6:
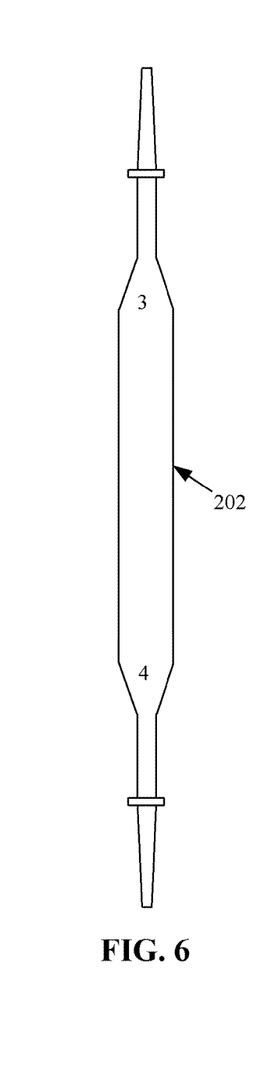
FIG. 6 illustrates a second double-ended osteotome of a set of double-ended osteotomes.
Figure 7:
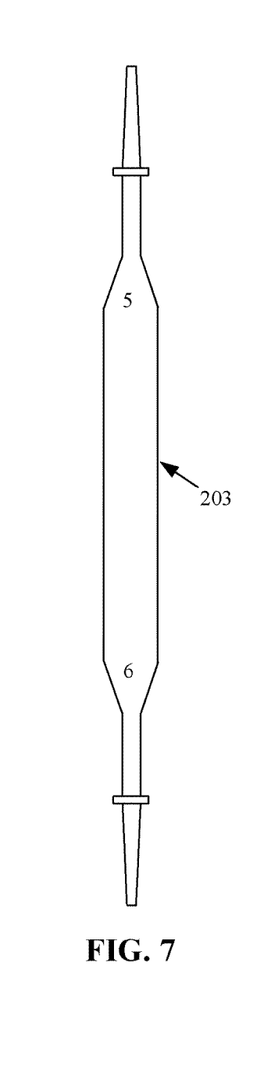
FIG. 7 illustrates a third double-ended osteotome of a set of double-ended osteotomes.
Figure 8:
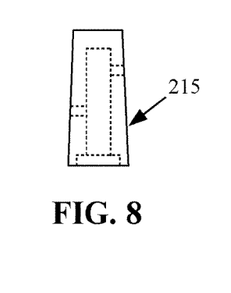
FIG. 8 illustrates a side view of a first embodiment of an impact cap usable with the double-ended osteotomes of FIGS. 5-7.
Figure 9:
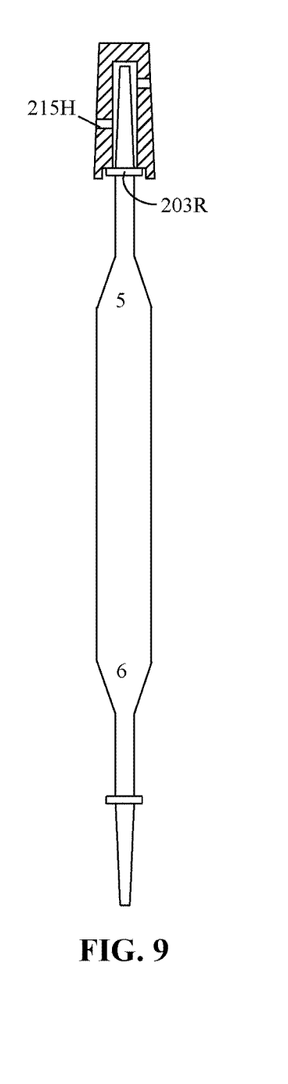
FIG. 9 shows a cut-away view of the impact cap of FIG. 8, positioned upon one end of the double-ended osteotomes of FIG. 7.
Figure 10:
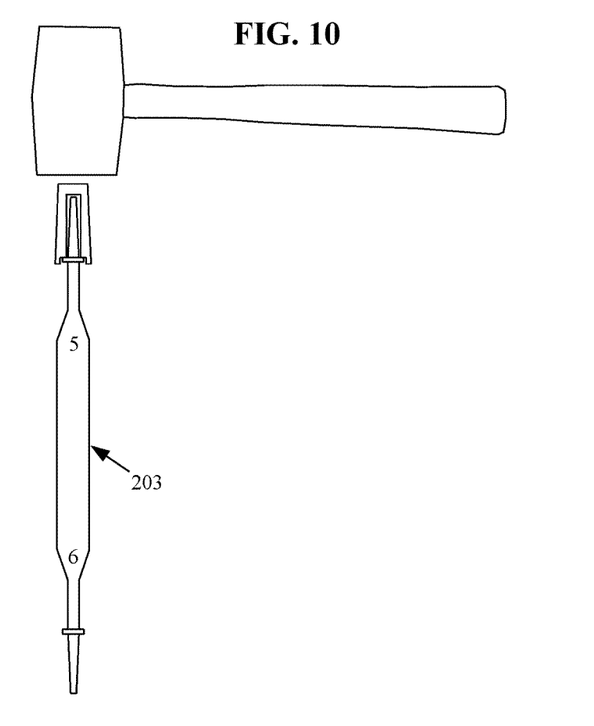
FIG. 10 illustrates a mallet being used to strike the impact cap positioned upon the double-ended osteotome, as shown in FIG. 9.

FIGS. 5-7 illustrate a set of osteotomes formed in accordance with another embodiment of the present invention. Each of the three osteotomes 201/202/203 shown in FIG. 5, FIG. 6. and FIG. 7 may be formed to be double ended, thus reducing by half the number of separate osteotome tools that may be required for the set. In order to be able to use a mallet on the exposed end of the double-ended osteotome, an impact cap 215, such as the one shown in FIG. 8, may be placed thereon, as seen in FIG. 9 and FIG. 10. The impact cap 215 may be formed with an internal opening large enough so that it may be properly seated upon any one of the ends of the double-ended osteotomes in the set, to contact and transmit force to the annular ring thereat (e.g., 203R), without any contact with the distal end of the tip that is to be used for socket formation. Also, the impact cap 215 may be formed with one or more holes 215H (see FIG. 9) to better accommodate thorough steam sterilization of the cap.

Figure 11A:
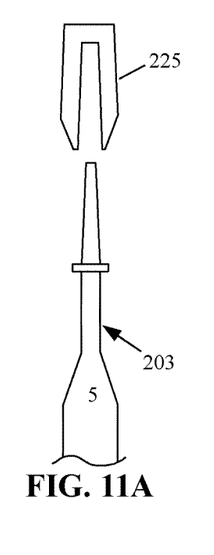
FIG. 11A illustrates a second embodiment of an impact cap, prior to being positioned upon one end of the double-ended osteotome of FIG. 7.
Figure 11B:
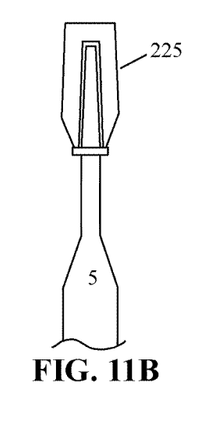
FIG. 11B illustrates the impact cap of FIG. 11A, after being positioned upon the end of the double-ended osteotome.
Figure 12A:
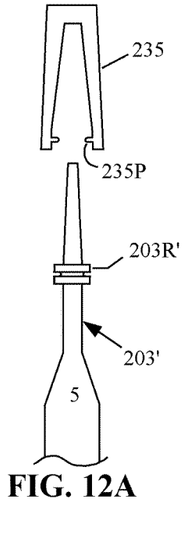
FIG. 12A illustrates a third embodiment of an impact cap, prior to being positioned upon one end of a double-ended osteotome of FIG. 7.
Figure 12B:
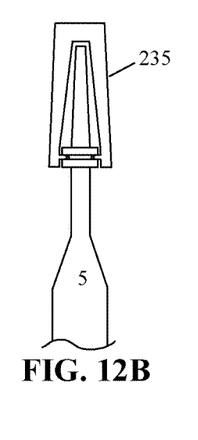
FIG. 12B illustrates the impact cap of FIG. 12A, after being positioned upon the end of the double-ended osteotome.
Figure 13A:
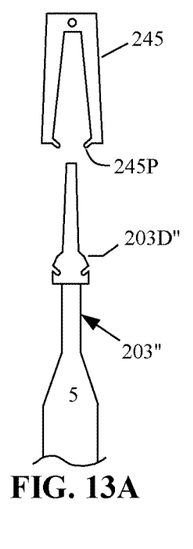
FIG. 13A illustrates a fourth embodiment of an impact cap, prior to being positioned upon one end of a double-ended osteotome of FIG. 7.
Figure 13B:
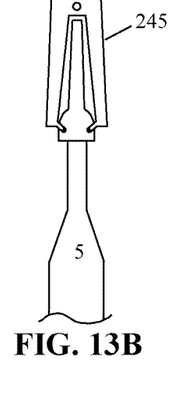
FIG. 13B illustrates the impact cap of FIG. 13A, after being positioned upon the end of the double-ended osteotome.

An alternate impact cap 225 is shown in FIGS. 11A-11B. Each of caps 215 and 225 may be formed of any suitable material, including, but not limited to, Teflon, and may be configured to freely slide onto and off of any of the ends of the double-ended osteotomes 201/202/203. The impact cap 235 shown in FIG. 12A is formed with an annular protrusion 235P that is configured to be received within an annular recess in the annular ring 203R' of the osteotome 203', as seen in FIG. 12B. Instead of the annular protrusion, external threading may be formed on the cap to threadably engage with corresponding internal threading that may be formed on the osteotome. The impact cap 245 shown in FIG. 13A is formed with an annular protrusion 245P that is canted with respect to the axis of the cap, and is configured to be received within an correspondingly shaped/oriented annular recess in the dome-shaped ring 203D" of the osteotome 203", as seen in FIG. 13B. The angled protrusion may be formed to be flexible, and may automatically deflect while being advanced along the dome shape until reaching the recess, without requiring use of a special tool, and may similarly be removed therefrom simply by applying an axial force in the opposite direction.

Figure 18:
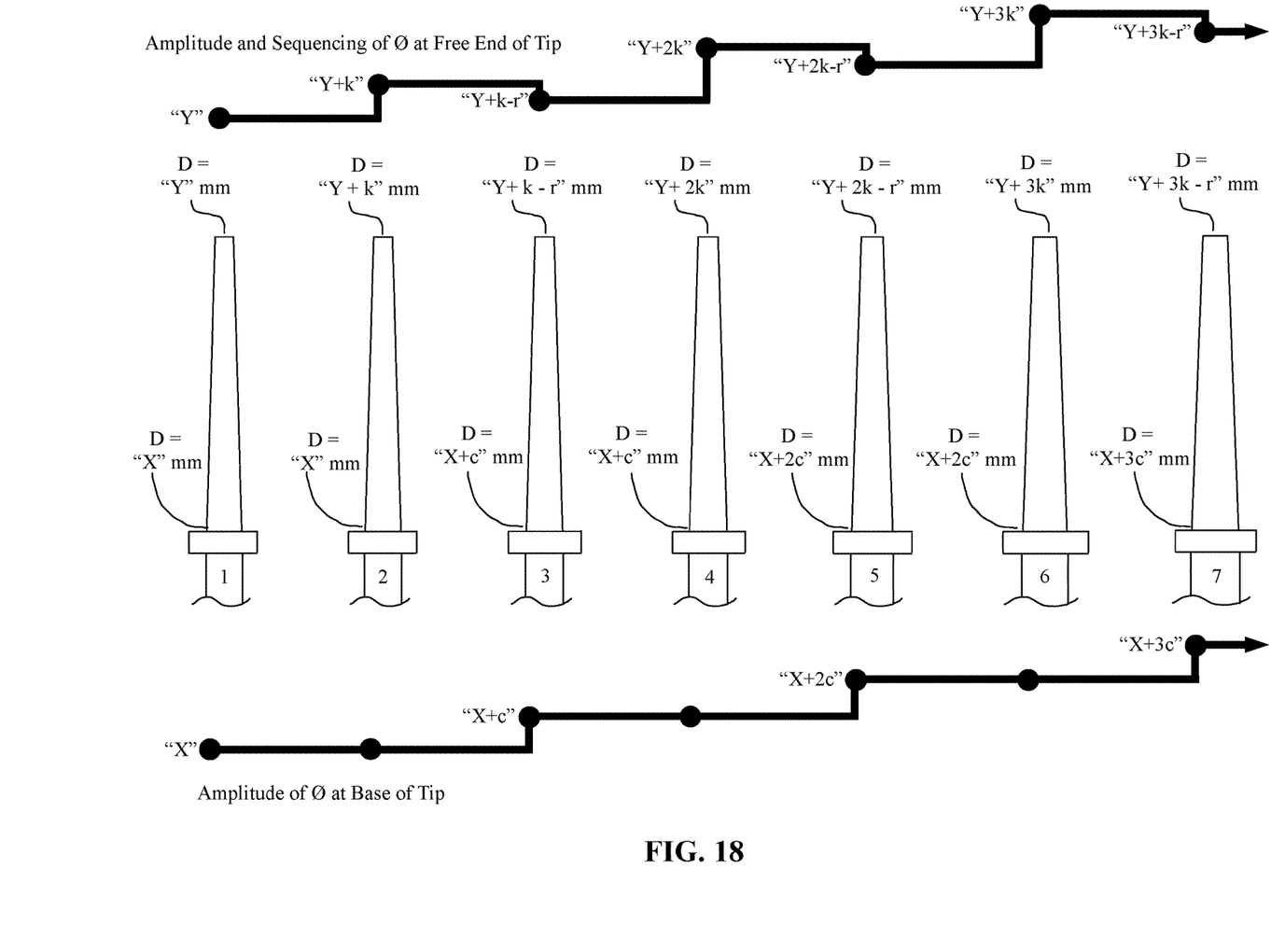
FIG. 18 illustrates a set of osteotomes that utilize a tip escalation scheme of the present invention, which creates alternating base to crest work (compression) areas in the dental implant socket during formation, with a stepped diameter escalation at the base of the tip, and an alternating step/regressive step escalation scheme at the free end.

FIG. 18 illustrates a set that includes a number, n, of osteotomes that are formed with tips that do not follow any of the prior art escalation schemes, and are particularly configured to further reduce stress during implant socket formation, and reduce the overall likelihood of a fracture.

Each of the osteotomes of the set have a conical working tip with a free end having a diameter $\phi_{An}$, and a working base having a diameter $\phi_{Bn}$. The first osteotome of the set (n=1) has a working tip formed with a first diameter, $\phi_{A1}$=Y. at the free end, and a second diameter, $\phi_{B1}$=X, at the base (i.e., at the full working depth), with the second diameter being larger than the first diameter, i.e., X>Y. The successive osteotomes of the set have a unique diameter escalation scheme.

The diameter at the free end of the tip alternately increases (i.e., the diameter increases by a constant increment "k" every other osteotome—that is for each even numbered osteotome—2, 4, 6, etc.), but the diameter at the free end may also regress (i.e., it decreases) between each such alternate diametrical increase (i.e., the diameter may decrease an amount "r" for each of the odd numbered osteotomes—3, 5, 7, etc.).

The diameter at the base of the tip (i.e., at its full working depth) alternately may increase by a constant increment, "c," i.e., it increases as a step function, with the diameter at the base of the tip increasing by an amount "c" for each of the odd numbered osteotomes—3, 5, 7, etc. These increases are illustrated within FIG. 18.

In one embodiment, the amount, r, that the diameter at the free end may regress may be in the range of 0.25 mm to 0.5 mm. In another embodiment, the amount, r, that the diameter at the free end may regress may be in the range of 0.1 mm to 0.2 mm. In yet another embodiment, the amount, r, that the diameter at the free end may regress may be in the range of 0.0 mm to 0.1 mm.

Figure 14:
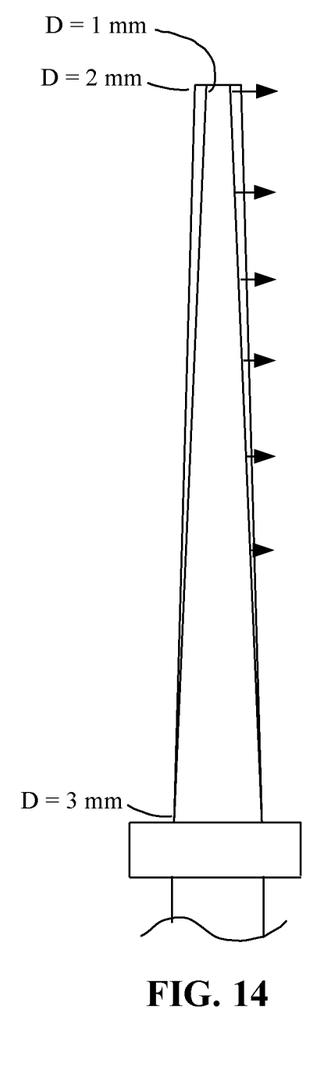
FIG. 14 illustrates a first osteotome tip having a second osteotome tip overlaid thereon, and having a 1 mm diameter escalation at the distal end of the tip, and an unchanged 3 nun base diameter.

The advantageous nature of this escalation scheme may be understood from FIGS. 14-17. FIG. 14 shows two osteotome tips overlaid, with the diameter at the base being the same, and with the diameter at the free end of the tip being escalated from 1 millimeter to 2 millimeters, in going from the first osteotome tip to the second osteotome tip. Use of these two tips for the first two osteotomes during implant socket formation provides for greater compression at the base of the alveolar ridge, and relatively insubstantial compression moving towards the crest of the ridge, which is illustrated graphically in FIG. 14 by the changing length of the arrows shown therein.

Figure 15:
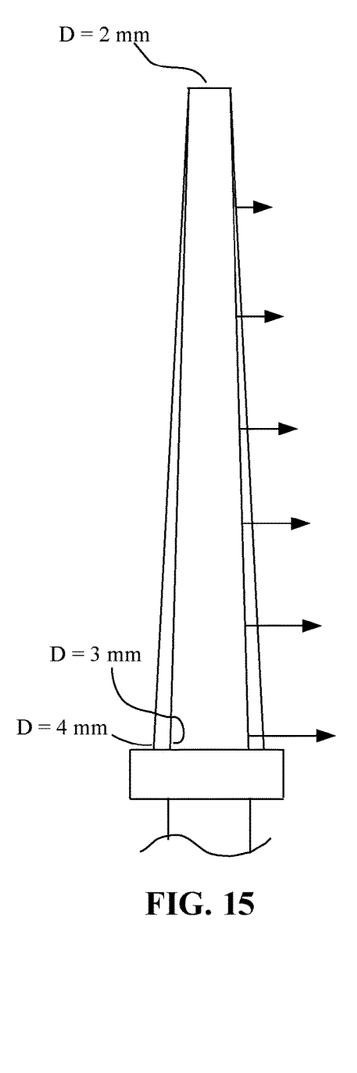
FIG. 15 illustrates a third osteotome tip overlaid upon the second osteotome tip of FIG. 14, having a 1 mm diameter escalation at the base of the tip, with an unchanged distal 2 mm (apical) diameter.
Figure 16:
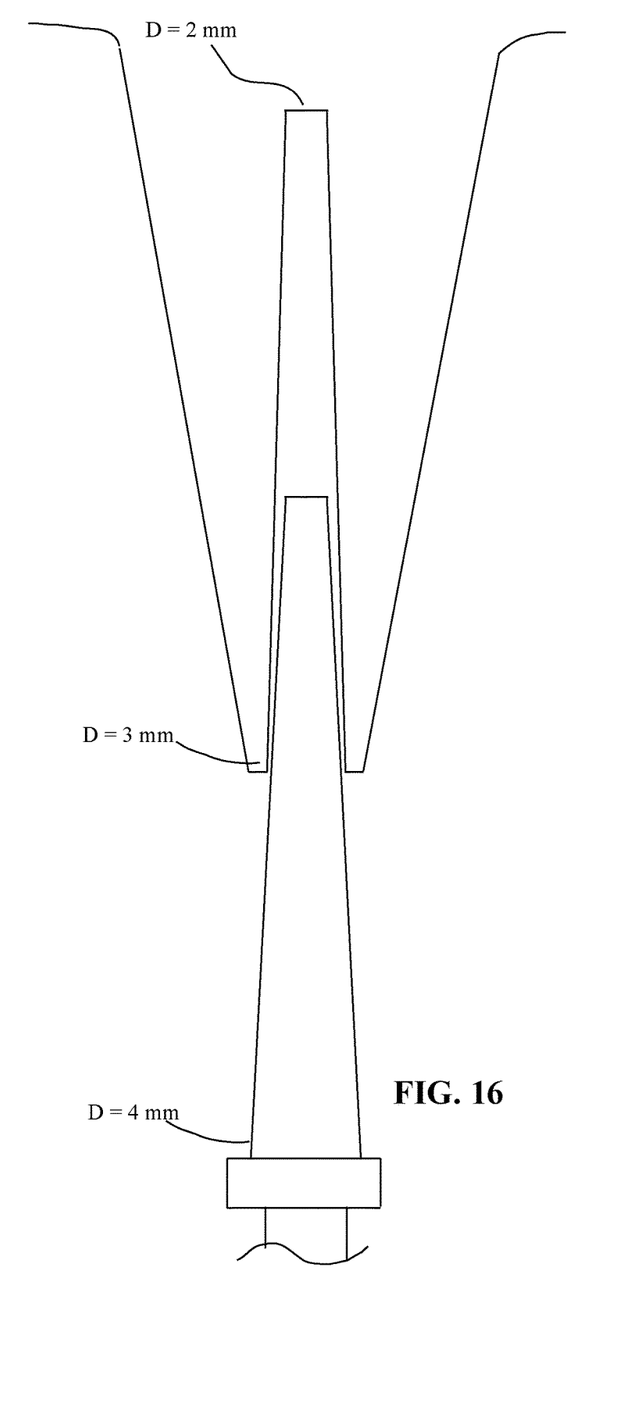
FIG. 16 illustrates insertion of the third osteotome tip of FIG. 15 into an implant socket previously worked by the second osteotome tip shown in FIG. 15.

A third osteotome tip is overlaid on the second osteotome tip in FIG. 15, in which the diameter at the base of the third osteotome tip has been escalated from 3 millimeters to 4 millimeters. Use of these two tips for the second and third osteotomes during implant socket formation provides for a substantial amount of compression at the crest of the alveolar ridge, which does not diminish appreciably in moving towards the bottom of the ridge (i.e., at the free end of the tip), which is illustrated graphically in FIG. 15 by the arrows shown therein. This means that as the third osteotome is initially inserted into the socket, as shown in FIG. 16, the crest will first be contacted, and have pressure applied thereto, which pressure will constantly increase as the osteotome is inserted further, and such pressure will by successively applied to increasingly deeper portions of the ridge.

Figure 17:
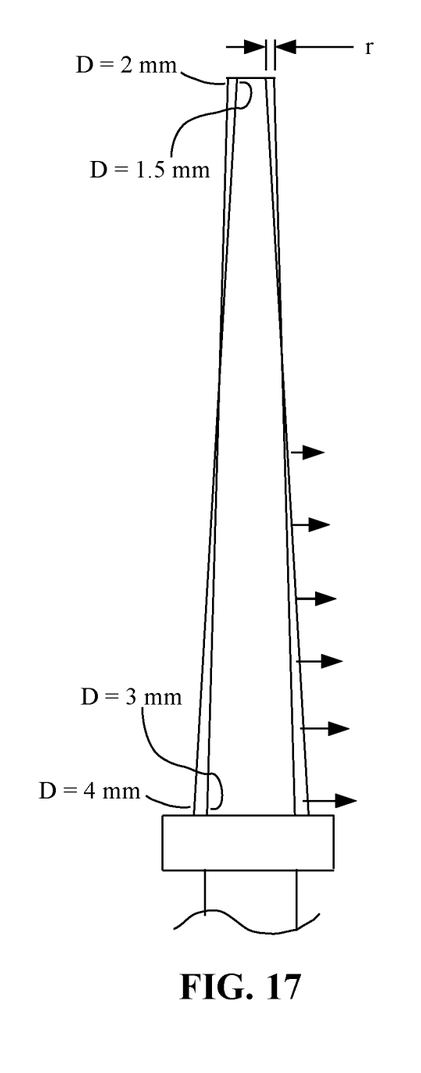
FIG. 17 illustrates a third osteotome tip in accordance with the present invention overlaid upon the second osteotome tip of FIG. 14, having a one millimeter base diameter escalation, with a corresponding regressive 1.5 mm diameter size at the distal end.

A more gradual escalation scheme is illustrated in FIG. 17, in which a third osteotome tip is overlaid over the second osteotome, where the diameter at the base of the third osteotome tip has been escalated from 3 millimeters to 4 millimeters, but the diameter at the free end of the tip has regressed from 2 millimeters to 1.5 millimeters. Use of these two tips for the second and third osteotomes during implant socket formation provides for zero compression at roughly the deepest half of the implant socket in the alveolar ridge, with an increasing amount of compression in moving from the middle of the socket towards the crest of the ridge (i.e., towards the base of the tip), which is illustrated graphically in FIG. 17 by the arrows shown therein. Therefore, only the shallowest half of the implant socket (that being closest to the crestal portion) is worked with the third osteotome, and only after the second osteotome had already been used to work the lower half of the implant socket to compress and thin the deep bone, to make it more flexible before using the third osteotome.

It should be noted that the osteotome tips disclosed herein may be used with motor driven devices, and as such, the tips may also have threads formed thereon.

While illustrative implementations of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A number of osteotomes, n, forming a set of osteotomes, for use during a ridge expansion osteotomy to reduce alveolar stress and to reduce likelihood of a fracture, each said osteotome of said set comprising a conical working tip with a free end having a diameter $\phi_{An}$, and a working base $\phi_{Bn}$; a first osteotome, n=1, of said set comprising said working tip formed with a first diameter, $\phi_{A1}=Y$, at said free end, and with a second diameter, $\phi_{B1}=X$, at said working base, said second diameter being larger than said first diameter, X>Y; and wherein for successive osteotomes of said set, said diameter at said free end increases as an alternate step and regressive step sequence, and said diameter at said working base alternately increases by a constant increment, c, as a step function.

2. The set of osteotomes according to claim 1, wherein when n=4 osteotomes in said set,
said diameter, $\phi_{An}$, at said free end of each said osteotome in said set is as follows:

$\phi_{A1}=Y$ $\phi_{A2}Y+k$ $\phi_{A3}=Y+k-r$ $\phi_{A4}=Y+2k$, and said diameter, $\phi_{Bn}$, at said base of each of said osteotome in said set is as follows:
ti $\phi_{B1}=X$ $\phi_{B2}=X$ $\phi_{B3}=X+c$ $\phi_{B4}=X+c$.

3. The set of osteotomes according to claim 2, wherein r is in the range of 0.25 mm to 0.5 mm.

4. The set of osteotomes according to claim 2, wherein r is in the range of 0.1 mm to 0.2 mm.

5. The set of osteotomes according to claim 2, wherein r is in the range of 0.0 mm to 0.1 mm.

6. The set of osteotomes according to claim 2, wherein k≠C.

7. The set of osteotomes according to claim 1, wherein when n=5 osteotomes in said set,
said diameter, $\phi_{An}$, at said free end of each said osteotome in said set is as follows:

$\phi_{A1}=Y$ $\phi_{A2}Y+k$ $\phi_{A3}=Y+k-r$ $\phi_{A4}=Y+2k$ $\phi_{A5}=Y+2k-r$, and said diameter, $\phi_{Bn}$, at said base of each of said osteotome in said set is as follows:
ti $\phi_{B1}=X$ $\phi_{B2}=X$ $\phi_{B3}=X+c$ $\phi_{B4}=X+c$ $\phi_{B5}=X+2c$.

8. The set of osteotomes according to claim 7, wherein r is in the range of 0.25 mm to 0.5 mm.

9. The set of osteotomes according to claim 7, wherein r is in the range of 0.1 mm to 0.2 mm.

10. The set of osteotomes according, to claim 7, wherein r is in the range of 0.0 mm to 0.1 mm.

11. The set of osteotomes according to claim 7, wherein k≠C, and r<k.

12. The set of osteotomes according to claim 1, wherein when n=6 osteotomes in said set,
said diameter, $\phi_{Bn}$, at said base of each said osteotome in said set is as follows:

$\phi_{A1}=Y$ $\phi_{A2}Y+k$ $\phi_{A3}=Y+k-r$ $\phi_{A4}=Y+2k$ $\phi_{A5}=Y+2k-r$ $\phi_{A6}=Y+3k$, and said diameter, $\phi_{Bn}$, at said base of each of said osteotome in said set is as follows:
ti $\phi_{B1}=X$ $\phi_{B2}=X$ $\phi_{B3}=X+c$ $\phi_{B4}=X+c$ $\phi_{B5}=X+2c$ $\phi_{B6}=X+2c$.

13. The set of osteotomes according to claim 12, wherein r is in the range of 0.25 mm to 0.5 mm.

14. The set of osteotomes according to claim 12, wherein r is in the range of 0.1 mm to 0.2 mm.

15. The set of osteotomes according to claim 12, wherein r is in the range of 0.0 mm to 0.1 mm.

16. The set of osteotomes according to claim 12, wherein k≠C, and r<k.

17. An osteotome comprising a conical tip, said conical tip comprising a first cross-cut formed substantially parallel to an axial direction of said tip, and extending from a distal end of said tip to terminate proximate to a full working depth of said tip; a first through-hole centered upon said termination of said first cross-cut, being oriented parallel to said first cross-cut and perpendicular to the axial direction of said tip; a second cross-cut formed substantially parallel to the axial direction of said tip, and being clocked, with respect to the axial direction, to be 90 degrees away from said first cross-cut, a second through-hole centered upon said termination of said second cross-cut, being oriented parallel to said second cross-cut and perpendicular to the axial direction of said tip; said first and second cross-cuts configured to result in four prongs at said distal end of said tip; said first through-hole and said second through hole comprising a diameter being larger than a width of said cross-cuts to permit flexure of said four prongs.

18. The osteotome according to claim 17, wherein each of said first cross cut and said second cross-cut terminate beyond a full working depth of said tip.

19. A combination osteotome and impact cap, said osteotome comprising a shaft configured to terminate at a first end thereof in a first conical working tip, and said shaft configured to terminate at a second end thereof in a second conical working tip, each of said first conical working tip and said second conical working tip comprising an annular ring; and said impact cap comprising a socket configured to receive a portion of said first conical tip or said second conical tip therein, and means for engaging said annular ring for transmitting force thereto and for preventing contact between said tip end and said impact cap.

20. The combination osteotome and an impact cap according to claim 19, further comprising one or more through holes into a base of said socket, for transmitting steam during sterilization of said impact cap.

* * * * *